United States Patent [19]

Goetz et al.

[11] Patent Number: 5,055,194

[45] Date of Patent: Oct. 8, 1991

[54] SUPPORT FOR HIGH PERFORMANCE LIQUID CHROMATOGRAPHY IN A MAGNETICALLY STABILIZED FLUIDIZED BED

[75] Inventors: Victor Goetz, Philadelphia; David J. Graves, Devon, both of Pa.

[73] Assignee: University of Pennsylvania, Philadelphia, Pa.

[21] Appl. No.: 387,073

[22] Filed: Jul. 28, 1989

[51] Int. Cl.⁵ .......................................... B01D 15/08
[52] U.S. Cl. .................................. 210/635; 210/656; 210/695; 210/198.2; 210/502.1; 210/222; 502/401; 502/402
[58] Field of Search ............... 210/635, 656, 695, 661, 210/679, 659, 198.2, 502.1, 503, 504, 222, 223; 502/402, 403, 401, 406; 55/67, 100, 386

[56] References Cited

U.S. PATENT DOCUMENTS

| | | | |
|---|---|---|---|
| 2,885,366 | 5/1959 | Iler | 252/313 |
| 3,219,318 | 11/1965 | Hershler | 259/1 |
| 3,439,899 | 4/1969 | Hershler | 259/1 |
| 3,440,731 | 4/1969 | Tuthill | 34/1 |
| 3,485,658 | 12/1969 | Iler | 117/69 |
| 3,505,785 | 4/1970 | Kirkland | 55/67 |
| 3,722,181 | 3/1973 | Kirkland et al. | 55/67 |
| 3,951,799 | 4/1976 | Weiss et al. | 210/695 |
| 4,016,149 | 4/1977 | Travis et al. | 210/635 |
| 4,115,927 | 9/1978 | Rosensweig | 34/1 |
| 4,247,987 | 2/1981 | Coulaloglou et al. | 34/1 |
| 4,261,109 | 4/1981 | Mikus et al. | 34/1 |
| 4,272,893 | 6/1981 | Levenspiel et al. | 34/1 |
| 4,283,204 | 8/1981 | Savage | 55/3 |
| 4,339,337 | 7/1982 | Tricot et al. | 210/679 |
| 4,411,789 | 10/1983 | Liburdy | 210/198.2 |
| 4,661,327 | 4/1987 | Horton | 210/679 |
| 4,675,113 | 6/1987 | Graves et al. | 210/635 |
| 4,780,113 | 10/1988 | Koslow | 210/661 |
| 4,855,045 | 8/1989 | Reed | 210/223 |
| 4,861,705 | 8/1989 | Margel | 210/661 |
| 4,919,804 | 4/1990 | Dorsey et al. | 210/502.1 |
| 4,935,147 | 6/1990 | Ullman et al. | 210/695 |
| 4,937,001 | 6/1990 | Bellows | 210/695 |

OTHER PUBLICATIONS

M. A. Burns & D. J. Graves, "Structural Studies of a Liquid-Fluidized Magnetically Stabilized Bed," 67 Chem. Eng'g Comm. 315 (1988).
P. Knight, "Refining Recombinant Products with Chromatography," 6 Bio/Tech. 726 (1988).
C. H. Lochmuller et al., "Fluidized-Bed Separators Reviewed: A Low Pressure Drop Approach to Column Chromatography," 1(1) Preparative Chrom. 93 (1988).
C. H. Lochmuller & L. S. Wigman, "Affinity Separations in Magnetically Stabilized Fluidized Beds: Synthesis and Performance of Packing Materials," 22(11) Sepa. Sci. & Tech. 2111 (1987).
M. A. Burns & D. J. Graves, "The Magnetically Stabilized Fluidized Bed as a Biochemical Processing Tool," 501 Annals N.Y. Acad. Sci. 103 (1987).
T. Hu & J. Wu, "Study on the Characteristics of a Biological Fluidized Bed in a Magnetic Field," 65 Chem. Eng'g Res. Des. 238 (May 1987).
J. Kohler & J. J. Kirkland, "Improved Silica-Based Column Packings for High-Performance Liquid Chromatography," 385 J. Chrom. 125 (1987).
C. H. Lochmuller & L. S. Wigman, "Aerosel-Jet Produced, Magnetic Carrageenan-Gel Particles: A New Affinity Chromatography Matrix," 40 J. Chem. Tech. Biotech. 33 (1987).
J. Kohler et al., "Comprehensive Characterization of Some Silica-Based Stationary Phases for High-Performance Liquid Chromatography," 352 J. Chrom. 275 (1986).
K. D. Lork et al., "Role of the Functional Group in n-Octyldimethylsilanes in the Synthesis of $C_8$ Reversed-Phase Silica Packings for High-Performance Liquid Chromatography," 352 J. Chrom. 199 (1986).
C. D. Scott, "Techniques for Producing Monodispersed Biocatalyst Beads for Use in Columnar Bioreactors," Oak Ridge National Lab. manuscript (1985).
M. A. Burns & D. J. Graves, "Continuous Affinity Chromatography Using a Magnetically Stabilized Fluidized Bed," 1(2) Biotech. Progress 95 (Jun. 1985).
M. A. Burns et al., "Dried Calcium Alginate/Magnetite Spheres: A New Support for Chromatographic Separations and Enzyme Immobilization," 27 Biotech. & Bioeng'g 137 (1985).
R. E. Rosensweig et al., "Magnetically Stabilized Fluidized Solids," 77(205) A.I. Ch. E. Sympo. Series 8 (1981).
R. E. Rosensweig, "Fluidization: Hydrodynamic Stabilization with a Magnetic Field," 204 Science 57 (Apr. 1979).
K. Unger & B. Scharft, "Controlled Porosity Silica Supports from Hydrolytic Polycondensation Reaction of Poly(ethoxysiloxane)," 55(2) J. Colloid. & Interface Sci. 377 (May, 1976).
R. K. Iler, "Relation of Particle Size of Colloidal Silica to the Amount of a Cationic Polymer Required for Flocculation and Surface Coverage," 37(2), J. Colloid. & Interface Sci. 364 (Oct. 1971).
J. J. Kirkland & J. J. DeStephano, "Controlled Surface Porosity Supports with Chemically Bonded Organic Stationary Phases for Gas and Liquid Chromatography," 8 J. Chroma. Sci. 309 (1970).
C. Horvath & S. R. Lipsky, "Column Design in High Pressure Liquid Chromatography," 7 J. Chroma. Sci. 109 (Feb. 1969).
R. K. Iler, "Multilayers of Colloidal Particles," 21 J. Colloid. & Interface Sci. 569 (1966).
R. E. Rosensweig, "Magnetic Stabilization of the State of Uniform Fludization", 18 Ind. & Eng'g Chem. Fundamentals 260 (Aug. 1979).

*Primary Examiner*—Stanley S. Silverman
*Assistant Examiner*—Cynthia L. Nessler
*Attorney, Agent, or Firm*—Woodcock Washburn Kurtz Mackiewicz & Norris

[57] ABSTRACT

A method of, and an apparatus for, conducting chromatographic separations of multi-component systems utilizing silica-coated, magnetically susceptible particles in an MSFB is disclosed. A support material comprised of beads having a magnetic core surrounded by a silica derivative porous coating is used.

28 Claims, No Drawings

SUPPORT FOR HIGH PERFORMANCE LIQUID CHROMATOGRAPHY IN A MAGNETICALLY STABILIZED FLUIDIZED BED

This invention was made with government support under grants awarded by the National Science Foundation. The United States government has certain rights in this invention.

BACKGROUND OF THE INVENTION

1. Field of the Invention

This invention relates to an improved support material for use in chromatography. More particularly, it relates to a magnetic support material usable for high performance liquid chromatography operated in a magnetically stabilized fluidized bed.

2. Description of the Prior Art

In recent years, there has been a growing awareness of separation costs as a part of the total cost in chemical processes. The biochemical separation processes currently used for enzyme and protein purification present further difficulties. At present, they are almost without exception highly labor-intensive, slow, and relatively non-selective. A typical separation would involve gel filtration, ion exchange, or selective adsorption in chromatography columns. The fragile beads used in such columns impose pressure drop limits of 1 psi or less with correspondingly low flow rates.

Another common but awkward step involves fractional precipitation of proteins followed by centrifugation and decantation. Separations based on electrical charge such as electrophoresis and isoelectric focusing offer relatively convenient ways of obtaining purified compounds at the laboratory level, but pose problems of scale up. These problems arise because the heat produced by the passage of electric current increases as the square of a dimension (i.e. as the cross section) while the surface area for heat removal goes up only linearly. Convection, band spreading, etc. also increase at high rates with increasing scale. Normally, one must stop the process and stain for proteins to see how far the separation has progressed. Attempts have been previously made to save some of the manual labor usually associated with such operations by arranging bio-separation units into a continuous processing train. Some of the units are inherently batch oriented, however, and these attempts serve only to enforce the notion that new purification techniques are needed.

Among the many techniques used today in biochemical separations, perhaps the most efficient and selective is one called affinity chromatography (AC). Unlike the other separation techniques mentioned, which have typical purification factors $P_f$ (=product purity/feed purity) of 2 to 10, affinity separations in favorable cases achieve $P_f$ values of 10,000 in a single step. Further, unlike other techniques, AC does not rely on general molecular properties such as size, electrical charge, or density to carry out a separation. Instead, it involves a very specific interaction between two biomolecules, one of which is chemically attached to a solid support phase and the other of which is dissolved in solution (usually aqueous). Such interactions are almost a universal feature of biomolecules. Specific examples would include binding between antibodies and antigens, hormones and receptors, enzymes and either substrates, coenzymes, inhibitors, or activators, DNA and its complement (a repressor or catabolite gene activator protein for double-stranded DNA or the complement of a single strand of DNA) and messenger RNA and ribosomes.

The beauty of such biochemical pairing is that since it involves a number of simultaneous interactions between amino acid or nucleotide residues, it can be highly specific. Biomolecules typically perform their functions in the presence of thousands of different types of molecules, indicating that this specificity is both a necessary and a natural part of their character. Affinity chromatography is a broad term that involves everything from a weak interaction, which simply retards one molecule's passage through a column, to a strong, almost nonreversible binding to the column packing. The latter would more properly be termed a bio-specific adsorption-desorption cycle. Drastic changes in pH, ionic strength, or temperature, or the addition of a competing soluble molecule are needed in such a case to release the molecule from its complement on the solid phase. This strong binding system could be operated in a batch vessel in an adsorption-desorption mode, but in most cases a column is used whether or not it is needed. Since other molecules are not usually affected by passage through the affinity column, several columns in series can be used to recover several molecules of interest from a given fermentation broth. The cost of such high specificity is a requirement for a new solid support for each product to be isolated. These chromatographic supports are the most expensive single component of the technique.

Despite the advantages over other bioseparation schemes, normal affinity chromatography still has several serious disadvantages: (1) Even when operated as a column, it is a discontinuous chromatographic or adsorption-desorption process characterized by the introduction of a "pulse" of material and the recovery of a usually diluted "pulse" of product. The disadvantage of this type of operation is that the size of the sample is severely limited. Most of the time that the column is in operation, no product is being collected, leading to an inefficient system. (2) One cannot, in such a column, use the viscous, debris-laden suspension of broken cells from a fermentation that one might hope to. A packed column would almost immediately plug if subjected to such a mixture. The removal of debris and DNA (whose extremely high molecular weight has a large effect on viscosity) is still a serious problem in industrial-scale processes. (3) Since peak emergence from the column is related to time, control and automation of the process is more difficult than it is for a steady-state operation.

Recognizing these shortfalls, attempts were made to overcome these problems by devising various types of continuous chromatographic techniques. The aim wa to eliminate the inefficiency of a batch operation by allowing the sample to be injected continuously, and the products to be continuously withdrawn. These techniques utilized a moving chromatographic bed wherein the movement (or in some cases a simulated movement) is either perpendicular to the solvent flow, allowing a number of different compounds to be purified simultaneously, or countercurrent to the flow, in which case usually only two pure components are obtained. The advantage of either variation is the relatively high throughput that can be obtained compared to repeated batch operations. The disadvantage of some of these techniques, such as the simulated moving bed, is that they require elaborate and expensive mechanical moving seals or automatic valves to operate. In addition to the added expense, the risk of contamination is high when the system is one involving biomaterials, and when it is operated over long periods of time. Also, the problem of clogging by debris is not eliminated by any of these continuous systems when they only simulate bed motion.

In addition to affinity chromatography, there exist several chromatographic techniques or "modes" such as normal phase, reversed-phase, hydrophobic interaction, ion-exchange, and size exclusion. The generic term chromatography refers to a separation process based on differential adsorption of individual components of a flowing feed mixture on a solid support such that different products emerge from a tube filled with an appropriate support at different rates. The varieties of chromatographic modes differ in the physical basis on which they accomplish the separation.

The other chromatographic modes cannot achieve the specificity of affinity interactions but, in exchange, offer a much more practical advantage—flexibility. Because these techniques rely on a product's tendency to partition unequally between two unlike phases, the same solid support can be used for many different separations with only the more readily modified mobile phase liquid composition adjusted to make the solid and liquid phases more or less distinct.

High Performance Liquid Chromatography (HPLC) has emerged as one of the dominant procedures used for bioseparations today. All of the chromatographic modes described above have been demonstrated in the HPLC system, which achieves extremely high separation efficiencies by employing small (5-50 $\mu$m), porous particles with high surface areas for adsorption. Because these small particles are packed into a fixed bed, however, very high pressure heads are required to move fluid through an HPLC column at a sufficient flowrate. High pressures have become such an accepted part of chromatographic dogma that the acronym HPLC is equally often translated High Pressure Liquid Chromatography as High Performance Liquid Chromatography.

A recent development that can be used to advantage to eliminate or substantially reduce the problem of clogging while retaining the other advantages of continuous chromatography is the magnetically stabilized fluidized bed (MSFB). The ordinary fluidized bed has been used in industrial processing for many years, mostly with catalytic particles that tend to foul or become poisoned, or where thermal effects are important. The basis of such beds is that, above a certain critical fluid velocity, small particles of a solid become suspended in a high velocity stream and the solids suspension acts much like a fluid, permitting it to flow out of the reactor for regeneration or replacement. If the fluid velocity is increased above the critical fluidization value, however, undesirable effects such as bubbling and slugging occur. These cause bypassing of reactants through the bed and can result in particle entrainment in the gas. Although these problems are less severe in beds fluidized with liquids rather than with gases, the fluidized particles still undergo a strong back-mixing process so that the bed behaves much like a continuous flow stirred-tank reactor. While this turbulence may be desirable for certain processes such as heat exchange, it would be highly detrimental to any type of chromatographic separation.

As early as 1961, Hershler experimented with magnetic fields applied to liquid metals and magnetically susceptible solids that had been fluidized. He reported in the patent literature (U.S. Pat. Nos. 3,219,318 and 3,439,899) that a magnetic field created with an alternating current could be used to stir such liquid metals, fluidize beds even in the absence of a supporting gas or liquid stream, and (with several isolated fields in a column) decrease the bubbling and prevent material from being ejected from the top of a fluidized bed.

Other work on magnetic fields in conjunction with fluidized beds was carried out by Tuthill (U.S. Pat. No. 3,440,731). It was not until the late 1970's, however, when Rosensweig began publishing in this area that careful and systematic study of magnetically stabilized fluidized beds began ("Magnetic Stabilization of the State of Uniform Fluidization," 18 Ind. & Eng'g Chem. Fundamentals 260 (Aug. 1979); "Fluidization: Hydrodynamic Stabilization With A Magnetic Field," 204 Science 57 (April 1979); and with Siegell, Lee, and Mikus, "Magnetically Stabilized Fluidized Solids," 77(205) A.I.Ch.E. Synpo. Series 8 (1981)). Rosensweig and his co-workers made several important findings. First, fluidization of magnetically susceptible solids can be stabilized in a uniform gradientless magnetic field in which the individual particles experience no net force. An axially-oriented field is preferred, although the orientation of the field is not crucial. Second, stabilization is observed over a wide range of field strengths and fluidization velocities, and the applicable ranges of the important variables have now been mapped out by Rosensweig. For most fluid velocities, when the bed is stabilized, a decrease in magnetic field strength will result in normal fluidization, while an increase will result in agglomeration of the solid particles. The effect of the magnetic field can be viewed roughly as creating a magnetic dipole in each particle that causes it to become "sticky" in a direction parallel to the field lines. This produces what amounts to chains of beads parallel to the axis of the bed.

The MSFB has properties that are almost an ideal combination of those exhibited by the fixed bed and the fluidized bed. Like the fixed bed, the MSFB permits fluid flow through it with essentially no backmixing. Therefore, the fluid phase can be efficiently contacted with a solid bed of adsorbent. With a long enough bed, the liquid theoretically could have solute removed down to a level that is in equilibrium with the solid phase entering the top of the bed.

Like the fluidized bed, the MSFB exhibits low pressure drop and the ability to have solids flow smoothly through the system under the influence of gravity, so that they can be removed at the bottom and regenerated for re-use. Clogging by debris is controllable, because the bed contents, along with debris that they filter out, can be continually removed and replaced. Unlike either system, however, the MSFB can create a continuous countercurrent contact of solids and liquid with almost perfect plug flow of the solids. The utility of countercurrent contact is analagous to the thousands of distillation towers now in use in petroleum and other industries that are dependent on countercurrent flow of a liquid and a vapor.

It would be very advantageous if chromatographic operations carried out in an MSFB could achieve high performance without the high pressure. The fixed solids geometry and lack of backmixing achieved in an MSFB are a crucial development required for successful elution chromatography under the low pressure conditions of a fluidized bed. Furthermore, the ability to move the solid as well as liquid phases in an MSFB allows truly continuous, countercurrent operation not feasible in a conventional, fixed-bed HPLC. Especially for process scale separations, high production rates are a critical design consideration. Continuous operation makes it possible to achieve required throughputs with slower flowrates that could allow more complete equilibration between the fluid and solid phases.

The development of such a novel bioseparation process, however, depends on the availability of a solid phase support material appropriate for use in the MSFB. The major properties required are magnetic susceptibility to facilitate stabilization, high surface area for maximal adsorption, well-defined and reproducible surface characteristics, small particle size for improved transport characteristics, and high density to prevent particle elutriation at higher flowrates.

Presently, only one type of support material is available for use in MSFB bioseparations, the dried calcium alginate/magnetite (CAM) beads described in U.S. Pat. No. 4,675,113 (Graves et al.). (An analogous support, which substitutes K-carragenan for alginic acid, was also recently reported. Lochmuller & Wigman, "Aerosol-jet Produced, Magnetic Carrageenan-gel Particles: a New Affinity Chromatography Matrix," 40 J. Chem. Tech. Biotech. 33 (1987).) Although appropriate for the affinity system previously demonstrated, these beads are too large (300-900 $\mu$m) and have too little accessible surface area for protein separations based on non-specific modes of chromatography. To achieve the system flexibility, it is necessary to use a porous material that is readily derivatized to generate surfaces known to be chromatographically effective and large in area.

A number of techniques have been reported for reducing the size of extruded supports of this type. These include vibration of the extrusion needle to induce Rayleigh instabilities in the viscous extruded stream, and aiming a jet of air at the needle tip. The former technique, which involves costly transducers, has been shown to be limited to a 600 $\mu$m minimum diameter (translating to 185 $\mu$m when dried). Although this represents an improvement over the original dried CAM beads, commercial HPLC supports range in size from 5-75 $\mu$m.

The air jet technique, while capable of producing droplets as small as 40 $\mu$m (12 $\mu$m dry), is unacceptable on the basis of the significant waste of raw materials in isolating the desired size fraction because of the accompanying particle size distribution of 40-600 $\mu$m. Further, the resulting particle size distribution is also highly sensitive to the exact alignment of the gel and air outlets, making reproducibility questionable.

On the other hand, conventional chromatographic supports are predominantly silica-based. Surface preparation generally involves attachment of silanes to the silanol-rich silica by wellstudied techniques that are easily found in the literature. Silanes are organosilicon compounds that feature a readily bondable silicon head group and a wide variety of organic tails that can provide the desired normal phase, reversed phase, hydrophobic or ion exchange surfaces desired for whichever chromatographic mode is to be used. Unfortunately, silica itself is not magnetically susceptible and, therefore, is not directly usable in an MSFB.

Accordingly, there exists a need for a support material, usable in an MSFB, that is of suitably small size for use in HPLC while avoiding the use of high pressure. The support should also involve a porous material that is readily derivatized to generate surfaces known to be chromatographically effective.

SUMMARY OF THE INVENTION

The present invention meets the need for a support material that is usable in an MSFB and that is of suitably small size for use in preparative HPLC. The present invention involves using beads having a magnetic and impervious core surrounded by a coating of porous silica that can be bound with various binding ligands. The magnetic core enables the beads to be used to advantage in an MSFB while the silica derivative coating enables a wide variety of chromatographic techniques to be used in order to separate out a variety of components from a multi-component system. Use of such beads in an MSFB used for HPLC results in efficient separation at very low pressure drops in comparison to normal HPLC methods.

Accordingly, it is an object of the present invention to disclose a novel magnetic chromatographic separation support material.

It is a further object of the present invention to disclose the use of a novel magnetic support material in HPLC of bioproducts and other multi-component systems.

It is still a further object of the present invention to disclose HPLC of bioproducts carried out in a magnetically stabilized fluidized bed.

DETAILED DESCRIPTION OF THE PREFERRED EMBODIMENTS

The following description and examples are presented in order to allow for a more thorough understanding of the subject matter and experimental procedure of the present invention. The examples are meant to illustrate the embodiments of the present invention, and are not to be construed as limiting the scope of the invention.

In 1969, a particular support structure called the pellicular bead was first described by Horvath and Lipsky, "Column Design In High Pressure Liquid Chromatography," 7 J. Chroma. Science 109 (Feb. 1969). The pellicular support concept utilizes an impermeable core coated with only a thin, porous active layer. The structure was originally proposed in order to minimize diffusion limitation in the large (75 $\mu$m) totally porous supports available at that time. Presently, however, in conventional HPLC, the pellicular bead has now largely given way to newer, small (5-10 $\mu$m) totally porous supports.

The present invention involves using the now-disfavored pellicular bead structure in an MSFB/HPLC system. Use of a pellicular bead structure in such a system provides two advantages: the enhanced transport characteristics of a pellicular bead can be utilized and, in addition, a magnetic material can be used as the impermeable core, thereby reaping the benefits of an MSFB. The porous surface coating is comprised essentially of silica, which allows the attachment of a wide variety of silanes by well-known techniques and, thereby, enables their use in a wide variety of chromatographic techniques.

Any variety of magnetically stabilized fluidized bed chromatography systems can be used in conjunction with the method of the present invention. The number of these alternative forms may be found in the prior art as, for example, U.S. Pat. No. 4,283,204 (Savage), U.S. Pat. No. 4,272,893 (Levenspiel et al.), U.S. Pat. No.

4,261,109 (Mikus et al.), U.S. Pat. No. 4,247,987 (Coulaglou et al.), and U.S. Pat. No. 4,115,927 (Rosensweig).

Typically, in operation, solid chromatographic support materials according to the present invention are introduced into a column bed, often in a small amount of solvent stream. A feed stream containing the crude bioproduct or other multi-component system to be separated enters the column at either end, but preferably at the bottom. Any standard means can be used for removing the solids from the bottom of the column and they can then be further treated to elute the bound biomaterial or separated component and can thereafter be recirculated if desired.

A simple embodiment of the apparatus of the present invention would involve a single column adsorbing and stripping off one component from the feed stream. It is clear, however, that any variety of such columns can be combined in series or otherwise to consecutively strip off and/or desorb various components. Another alternative would be to adsorb several components in a primary column and then desorb each of those components separately.

The core material can be just about any magnetic metal or magnetic metal oxide. Preferably, however, the material used will demonstrate magnetic properties when placed in a magnetic field but will avoid becoming permanently magnetic. Support materials that retain a permanent magnetism may cause problems of agglomeration upon removal from the MSFB.

It may be advantageous to use a paramagnetic or super-paramagnetic material in manufacturing the cores. In general, the magnetic materials used will have a higher density than the silica material used in normal HPLC. A further advantage of the beads of the present invention is that their density can be changed independently of their porosity.

The example of the preparation of a support material in accordance with the present invention discussed below is intended merely as a single embodiment of the present invention and should not be considered to limit the scope thereof. Those of ordinary skill in the art will recognize that a wide variety of magnetic materials can be substituted for the nickel of the disclosed embodiment without departing from the scope of the present invention.

A nickel/silica composite support can be produced by an electrostatic layering technique first discussed in R. K. Iler, "Multilayers of Colloidal Particles," 21 J. Colloid. & Interface Sci. 569 (1966), and put into commercial practice as disclosed in U.S. Pat. No. 3,505,785 (Kirkland), in the development of Du Pont's Zipax TM pellicular support, both of which references are incorporated herein.

In general, by virtue of its surface hydroxyl groups, silica carries a negative charge. A thin oxide coating on the nickel, as would be present on most metals, renders the nickel positively charged in aqueous solution. After cleaning with chloroform to remove any organics that adsorbed from the air, the nickel powder is immersed in a solution of colloidal silica (for example Ludox TM ). A monolayer of the anionic colloidal silica microparticles deposits on the nickel powder, reversing the charge and preventing further deposition. The remaining silica is then rinsed out of the reaction vessel and replaced with a cationic polymer solution that also lays down in a monolayer and reverses the surface charge. Such aqueous solutions of cationic polymers are commercially available as flocculating agents intended for water purification applications. (For example, Mirapol TM AD-1 (Miranol, Inc.), or C-Floc 9 TM (Cosan Chemical Corp.).)

The silica and polymer treatments can be continued in alternate steps to produce any desired number of layers. The number of layers would optimally be chosen to maximize the use of the transport characteristics of the porous silica as a chromatographic support material. The pores formed as the colloidal silica microparticles are deposited on the surface of the bead particles would be of the same order of magnitude as the silica microparticle size. Therefore, the desired pore size can be controlled by proper selection of the colloidal silica, which is typically commercially available from 10-100 nm.

For use in an MSFB, there is a trade-off between the weight of the prepared macroparticle beads and the effective distance that a molecule to be separated must penetrate. If the beads are too small (approximately less than 5 μm), the liquid phase will wash the particles out of the column if operated at any usable flow rate. If they are too large, the interior of the bead is not effectively used. Thus, since a minimum diameter/weight is required for adequate penetration, the method of the present invention makes use of pellicular bead technology to achieve a thin active layer while maintaining a large enough size to retain the material in the column.

It is preferred that the macroparticle beads be approximately 10-250 μm in diameter. The coating on these beads would typically be a very small fraction of the overall bead diameter, less than 10 μm and preferably less than about 3 μm. The thickness of the coating is determined by the efficiency of diffusion. Beyond a certain thickness, the inner portion of the coating will be underutilized.

In preparing the coating, the number of silica layers laid down will generally range up to approximately 100, depending upon the size of the colloidal silica microparticles being used.

Once the desired number of layers is obtained, the beads are heated to a temperature sufficient to burn out the polymer and partially sinter the silica. When the polymer is burned off by heating, a chemical reaction is generated between the various silica layers that overcomes the initial electrostatic repulsion that had prohibited direct layering of silica to silica. This step must be performed carefully, however, to prevent oxidation of the underlying nickel and accompanying breakage of the silica coating as the underlying porous nickel oxide grows outward from the original silica/nickel interface. A temperature of approximately 400° C. in air appears to efficiently remove the polymer without significant nickel oxidation. The sintering step can then be carried out in vacuum or in inert atmosphere at higher temperatures.

One problem that may be encountered when heating the silica/polymer coating to burn out the polymer and sinter the silica is that the magnetic core may expand at a faster rate causing cracks in the silica coating. Thus, it is preferable to use a core material having a low coefficient of expansion or one with a coefficient of expansion similar to that of the silica coating. One promising material is Invar TM (International Nickel Company), an alloy of nickel and iron or cobalt. As an alternative, the nickel particle can be protected from oxidation and other chemical attack by laying down a layer of, for example, gold before coating with silica.

The heat treatment is known to dehydrate the silica surface. However, since derivatization with silanes to prepare the chromatographic support surface requires surface hydroxyl groups, the surface will have to be rehydroxylated by acid or base treatment in a subsequent step. There is evidence that such a treatment is actually an advantage in that such rehydroxylation produces a fresh, uniform energy surface for silane attachment. (See, e.q., J. Kohler and J. J. Kirkland, "Improved Silica-based Column Packings for High-Performance Liquid Chromatography," 385 J. Chrom. 125 (1987).)

Once the magnetic core/silica composite macroparticle support has been prepared, it can be readily derivatized by the attachment of silane binding ligands using a wide variety of well-studied studied techniques known to those of ordinary skill in the art. An example of such techniques is disclosed in U.S. Pat. No. 3,722,181 (Kirkland et al.). Such silanes will feature a wide variety of organic tails that than can be used with various chromatographic modes.

In a particular example, 20–45 $\mu$m nickel particles were used as the core material. The use of such a dense metal serves a secondary function, that of a dense ballast. This density increases the terminal velocity of the particles in an MSFB and, thereby, extends the useful range of flow velocities in such an MSFB. In such a manner, adsorption surface area is maximized without bed instability or particle elutriation.

A summary of the support properties of a particular example preparation of the nickel/silica in comparison to commercial supports and the previously developed calcium alginate beads is shown in the following table

| Support Type | Particle Diameter (microns) | Specific Surface Area ($m^2/g$) | Density Normalized Area ($m^2/cc$) | Pore Volume (cc/g) | Average Pore Diameter (angstroms) |
|---|---|---|---|---|---|
| Alginate | 300–900 | 23–36 | 51–79 | 0.1 | 125 |
| Nickel/Silica | 20–45 | 10–12 | 84–106 | 0.035 | 125 |
| Commercial | 25–38 | 14 | 28 | 0.024 | 60 |
| Pellicular | 20 | 0.9 | 1.8 | 0.023 | 380 |
| Commercial | 5–10 | 90–130 | 99–143 | 0.6–1.6 | 300 |
| Totally Porous | 5–10 | 450 | 495 | 0.8 | 80 |

It should be noted that, while the specific disclosure given above discusses the layering of silica onto the magnetic core using a method of alternating silica layers with polymer layers followed by a burning off of the polymer material, any method of depositing suitable thicknesses of silica can be used. As an alternative example, Unger and Scharf have disclosed a method of beginning with a soluble silica material that is polymerized onto a surface using an organic filler emulsion that subsequently will evaporate off. This method avoids the heat treatment step but also lacks the ability to control the pore size as precisely as the Du Pont technique. K. Unger & B. Scharf, "Controlled Porosity Silica Supports From Hydrolytic Polycondensation Reaction of Poly(ethoxysiloxane)," 55(2) J. Colloid. & Interface Sci. 377 (May, 1976).

While the primary ingredients of the beads of the present invention are the magnetic core and the silica derivative outer coating, several other aspects may be important. It is known to those of skill in the art that a molecular layer of metal oxide is required on the surface of the core material in order to bind with the silica of the coating. Virtually all magnetic materials will naturally encompass a surface layer of oxide and thus would be suitable core materials.

In addition, it is preferable to provide an intermediate coating of a non-porous silica, or other material such as gold, between the core material and the silica derivative outer coating. Such a non-porous intermediate coating protects the components being separated from possible contamination by the metal of the magnetic core during their diffusion into the silica derivative outer coating. Such an intermediate layer also minimizes oxidation problems that can lead to cracking during the polymer burn-off step of bead production.

An intermediate coating of non-porous silica or other material can be deposited by any appropriate method as a pretreatment step to the forming of the porous outer coating. One example of a method of laying down such an intermediate coating is set forth in U.S. Pat. No. 2,885,366 (Iler), incorporated herein by reference.

Thus, one preferred embodiment of the support material to be used with the method and apparatus of the present invention is one having an Invar TM core with an oxide surface surrounded by a non-porous silica or gold coating and further surrounded by a porous silica coating coupled with a silane having an appropriate bonding ligand.

The magnetic beads can be used to great advantage in an MSFB operating to perform HPLC. Using such beads according to the method of the present invention provides at least the following advantages:

High Surface Area—as compared to the dried calcium alginate beads of the prior art, the beads of the present disclosure have a substantially improved surface area to volume ratio.

Controllable Surface Area and Pore Size—the ability to coat the magnetic core with a specifically chosen number of silica layers of a specifically chosen colloidal silica size enables the surface area of the beads to be much more accurately controlled. Further, by choice of the colloidal silica size, the pore size of the resulting coating can also be accurately controlled. The pore size will roughly correlate to the size of the colloidal silica chosen as will the thickness of each layer.

Versatility—since silica is used as the coating material, the extensive knowledge of the art with respect to methods for derivatizing silica is available and binding ligands capable of binding with one or more components of a multi-component system can be attached. Thus, the method is presently useful for a wide variety of separations and can be used in most HPLC modes, such as ion exchange, normal mode, and reverse phase in addition to affinity. (It is possible that the method of the present invention will not be readily usable in size exclusion HPLC due to the increased voids created in an MSFB.)

Durability—while polysaccharides such as calcium alginate tend to be attacked by bacteria, the beads of the present invention will not suffer from this problem. Silica also does not need to be pre-swelled as does, for example, Sepharose TM (Pharmacia Corp.)

Bead Size—as stated, the beads of the present invention can be produced in any size. By contrast, the calcium alginate beads of the prior art are relatively large and, therefore, are not as efficient.

On the other hand, while the beads currently used in normal HPLC techniques can be very small, normal HPLC can not be run on a continuous basis. Further, the small bead size of the normal packed HPLC column leads to a significant pressure differential across the column, typically approaching 2,000 psi per 20 cm of length.

Use of an MSFB, however, leads to a very significant reduction in pressure drop across the column. The method of the present invention can be operated with pressure drops of only 0.1–10 psi, typically less than 1 psi/cm. The pressure required in the present invention is roughly equal to the pressure needed to support the weight of the solid material and thereby fluidize the bed.

Efficiency—the use of an MSFB also allows for a continuous process whereby a feed stream to be separated, as well as a stream of solid support material can both be continuously fed to the HPLC column and support material bound with the component to be separated can be continuously removed from the other end of the column for further processing.

At the present time, it has been seen that the method of the present invention can achieve an efficiency of up to 6,000 plates/meter. It is anticipated that the efficiency can be significantly increased with further study. Thus, while the method of the present invention may not be as efficient on a per length basis as normal HPLC (due to the larger size of the support material beads and the increased void volume in a fluidized bed as compared to a packed bed), the present invention overcomes the inherent inefficiency of the batch process required with normal HPLC.

While various embodiments of the present invention have been illustrated and described, it is to be understood that this invention is capable of variation and modification and is not to be limited except to the scope of the appended claims.

What is claimed is:

1. A method of conducting chromatographic separations of multi-component systems comprising contacting a multi-component system contained in a liquid carrier fluid with a solid support contained in a magnetically stabilized, fluidized support bed, wherein the solid support comprises a plurality of generally spherical beads having a generally central magnetic core and a surrounding exterior coating about the core comprising a porous silica or silica derivative, said magnetic core having a coefficient of expansion similar to or less than the coefficient of expansion of said porous silica or silica derivative.

2. The method of claim 1 wherein the central core of the generally spherical beads is comprised of an impervious paramagnetic or superparamagnetic material.

3. The method of claim 1 wherein the central core of the generally spherical beads is comprised of an alloy of nickel and iron or an alloy of nickel and cobalt.

4. The method of claim 1 wherein the generally spherical beads further comprise an intermediate, non-porous coating comprised essentially of silica, gold or other protectively material.

5. The method of claim 1 wherein the exterior coating of the generally spherical beads further comprises a binding ligand capable of binding with one or more of the components of the multi-component system.

6. The method of claim 1 wherein the generally spherical beads have a diameter of about 10–250 μm.

7. The method of claim 1 wherein the exterior coating of the generally spherical beads is less than 10 82 m thick.

8. The method of claim 1 wherein the chromatographic technique used is affinity chromatography.

9. The method of claim 1 wherein the chromatographic technique used is ion exchange, normal mode, or reverse phase chromatography.

10. The method of claim 1 wherein the thickness of the exterior coating of the generally spherical beads is chosen to maximize the efficiency of the chromatographic technique.

11. The method of claim 1 wherein the pressure drop across the support bed is less than 1 psi/cm length.

12. The method of claim 1 further comprising adding support material to the top of the bed, moving the support material downwardly through the bed, and removing the support material from the bottom of the bed.

13. The method of claim 12 further comprising stripping or desorbing any components that have become bound to the support material after the support material is removed from the bed.

14. The method of claim 1 wherein the exterior coating is comprised of a plurality of like monolayers of like inorganic microparticles consisting essentially of silica irreversibly joined to and surrounding said central core, each of said monolayers having a thickness of one microparticle.

15. The method of claim 14 wherein the size of the microparticles is chosen to optimize the size of pores formed in the exterior coating.

16. The method of claim 14 wherein the central core includes an oxide layer on its surface that facilitates the joining of the core to the exterior coating.

17. A method of conducting High Performance Liquid Chromatography comprising contacting a multi-component liquid solution to be separated with a solid support contained in a magnetically stabilized, fluidized support bed, wherein the solid support comprises a plurality of generally spherical beads having a generally central magnetic core and a surrounding exterior coating about the core comprising a porous silica or silica derivative, said magnetic core having a coefficient of expansion similar to or less than the coefficient of expansion of said porous silica or silica derivative.

18. The method of claim 17 wherein the generally spherical beads are pellicular beads.

19. The method of claim 17 wherein the central core is comprised of an impervious paramagnetic or superparamagnetic material.

20. The method of claim 17 wherein the central core is comprised of an alloy of nickel and iron or an alloy of nickel and cobalt.

21. The method of claim 17 wherein the generally spherical beads further comprise an intermediate, non-porous coating comprised essentially of silica, gold, or other protective material.

22. The method of claim 17 wherein the exterior coating further comprises a binding ligand capable of binding with one or more components to be separated from said solution.

23. The method of claim 17 wherein the generally spherical beads have a diameter of about 10–250 μm.

24. The method of claim 17 wherein the exterior coating of the generally spherical beads is less than 10 μm thick.

25. The method of claim 17 wherein the exterior coating is comprised of a plurality of like monolayers of like inorganic microparticles consisting essentially of silica irreversibly joined to and surrounding the central core. each of the monolayers having a thickness of one microparticle.

26. The method of claim 17 further comprising adding support material to the top of the bed. moving the support material downwardly through the bed. and removing the support material from the bottom of the bed.

27. The method of claim 26 further comprising stripping or desorbing any components that have become bound to the support material after the support material is removed from the bed.

28. A method of conducting chromatographic separations of multi-component systems comprising:
  contacting a multi-component system with a solid support wherein the solid support is continuously fed to the top of a magnetically stabilized fluidized bed and continuously removed from the bottom of the bed. the solid support comprising a plurality of generally spherical beads having
  a generally central magnetic core that is 10-250 $\mu$m in diameter.
  an intermediate. non-porous coating comprised essentially of silica. gold. or other protective material, and
  a surrounding exterior coating that is less than 10 $\mu$m thick comprising a porous silica or silica derivative
  having a binding ligand capable of binding with one or
  more of the components of the multi-component system wherein the magnetic core is comprised of a material having a coefficient of expansion similar to or less than the coefficient of expansion of said porous silica or silica derivative.

* * * * *

UNITED STATES PATENT AND TRADEMARK OFFICE
CERTIFICATE OF CORRECTION

PATENT NO. : 5,055,194
DATED : October 8, 1991
INVENTOR(S) : Goetz et al.

It is certified that error appears in the above-identified patent and that said Letters Patent is hereby corrected as shown below:

Column 2, Line 54, change "wa" to --was--.

Column 7, Line 51, change "Zipax TM" to --Zipax™--.

Column 7, Line 60, change "Ludox TM" to --Ludox™--.

Column 8, Line 2, change "9 TM" to --9™--.

Column 8, Line 64, change "Invar TM" to --Invar™--.

Column 9, Line 16, after "well-studied" delete "studied".

Column 10, Line 25, change "Invar TM" to --Invar™--.

Column 10, Line 64, change "Sepharose TM" to --Sepharose™--.

Column 11, Line 50, after "less" delete "that".

Column 11, Line 62, change "protectively" to --protective--.

Column 12, Line 2, change "82" to --µ--.

Signed and Sealed this

First Day of June, 1993

Attest:

Attesting Officer

MICHAEL K. KIRK

Acting Commissioner of Patents and Trademarks